US008072466B2

(12) United States Patent
Harder et al.

(10) Patent No.: US 8,072,466 B2
(45) Date of Patent: Dec. 6, 2011

(54) MEDICAL EXAMINATION APPARATUS FOR ACQUIRING SLICE IMAGES OF A SUBJECT

(75) Inventors: Martin Harder, Nürnberg (DE); Christian Köglmeier, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1583 days.

(21) Appl. No.: 11/126,638

(22) Filed: May 11, 2005

(65) Prior Publication Data

US 2005/0261567 A1 Nov. 24, 2005

(30) Foreign Application Priority Data

May 13, 2004 (DE) ......................... 10 2004 023 849

(51) Int. Cl.
*G09G 5/00* (2006.01)

(52) U.S. Cl. ......... 345/619; 715/964; 382/132; 382/131

(58) Field of Classification Search .................. 345/619; 715/964; 382/131, 132
See application file for complete search history.

(56) References Cited

U.S. PATENT DOCUMENTS 6,056,556 A * 5/2000 Braun et al. .................. 434/323
2002/0081009 A1* 6/2002 Licato et al. .................. 382/131
2002/0082494 A1* 6/2002 Balloni et al. ................ 600/410

FOREIGN PATENT DOCUMENTS

EP 1 220 154 7/2002

OTHER PUBLICATIONS

Visio 2000, 1999, Visio Corporation. p. 23-24, 108.*

* cited by examiner

*Primary Examiner* — Michelle K Lay
(74) *Attorney, Agent, or Firm* — Schiff Hardin LLP

(57) ABSTRACT

A medical examination apparatus for acquisition of slice images of an examination subject, such as a magnetic resonance apparatus, has a control device for controlling the image acquisition procedure having at least one associated monitor on which graphic elements serving for adjustment of the image acquisition modalities can be displayed. The graphic elements can be positioned by the user via an input unit with regard to the image simultaneously displayed on the monitor. The control device controls the image acquisition procedure dependent on the position and type of the graphic elements. Some of the displayed graphic elements can be coupled to one another as needed in terms of their positional relationship so that, given a position change of a selected graphic element, all graphic elements coupled therewith can mutually be moved with retention of their positional relationship with one another.

13 Claims, 3 Drawing Sheets

MR Scanner
2
1
3
Control Device
Input Unit
6
5b
5a
a)
5b
Monitor
4

MR Scanner
2
1
3
Control Device
Input Unit
6
5b
5a
a)
5b
Monitor
4

11
10
11
11
10
11

13
13
13
12
13a
13b
13b
12
13a

MEDICAL EXAMINATION APPARATUS FOR ACQUIRING SLICE IMAGES OF A SUBJECT

BACKGROUND OF THE INVENTION

1. Field of the Invention

The present invention concerns a medical examination apparatus for acquisition of slice images of an examination subject, in particular a magnetic resonance apparatus, of the type having a control device that controls the image acquisition procedure, with at least one associated monitor on which can be displayed graphic elements serving for setting the image acquisition parameters, the graphic elements being positionable by the user via an input unit with regard to an image simultaneously displayed on the monitor, the control device controlling the image acquisition operation dependent on the position and type of the graphic elements.

2. Description of the Prior Art

Magnetic resonance or computed tomography systems are used primarily for acquisition of slice images of an examination subject. In order to be able to exactly set the image acquisition parameters, previously acquired overview slice images that show the examination subject are displayed to the physician or to the technician on one or more monitors. One or more graphic elements then are superimposed in this image. These graphic elements may be of different types and allow the image acquisition parameters to be defined and individually adjusted by the physician. The graphic elements, for example, can more specifically define the site of the image acquisition, thus the examination site, for example 2D and 3D slice elements that determine the position and orientation of the slice to be acquired, or volume elements or spatial grids (for example for CSI spectroscopy (CSI=Chemical Shift Imaging)). In addition, the graphic elements can be positioned, so that, for example, specific regions visible in the displayed overview images can be virtually masked out; these regions then are saturated in the imaging procedure, which can be defined by corresponding saturation elements.

Depending on the examination method or on the examination subject, it may be necessary for a particular measurement or a measurement task (measurement protocol) to position a number of graphic elements, these being primarily aligned in three-dimensional patient space to the anatomy of the patient (defined, for example, by three previously-acquired overview images that are orthogonal to one another). These graphic elements simultaneously must be aligned among one another in a fixed spatial relationship (for example parallel to each other with predetermined separation, perpendicular to each other with a common center point, at a predetermined angular ratio to each other, etc.). The graphic elements are to be positioned separately by the physician, i.e. the physician designs the measurement task or the measurement protocol virtually step-by-step by positioning the individual graphic elements. If, for example, after concluding positioning the physician determines the selected arrangement is to be changed, this causes every graphic element to be separately repositioned, which is very laborious and time-consuming because many individual manual steps have be re-executed. Even small variations involve a series of corrections to objects to be aligned relative to one another, but it is essential that this be done to achieve a meaningful image acquisition.

SUMMARY OF THE INVENTION

An object of the present invention is to provide a medical examination apparatus that allows a simple adjustment of the image acquisition parameters using the graphic elements.

This object is achieved in accordance with the invention by an examination apparatus of the type initially described wherein at least some of the displayed graphic elements can be coupled, as needed, to one another with regard to their position relationship, such that given a position change of a selected graphic element all graphic elements coupled with it can be moved as well while retaining their position relationship to one another.

The inventive examination apparatus offers the physician the possibility to couple with one another the graphic elements shown on the monitor and, for example, already positioned by the physician. This coupling can occur as needed via a suitable input unit, thus to "freeze" their position relationship relative to one another and to form an element group that is moved in its entirety given a correction involving a position change of a selected graphic element within the group, so that the position relationship of all coupled elements is maintained. The coupled graphic elements can be interactively, arbitrarily positioned by the user after a designated coupling. Because the coupling can be effected as needed, the physician can consequently arbitrarily position the graphic elements as before with regard to the measurement he desires; but necessary changes can be very quickly implemented because the laborious repositioning of all individual graphic elements is avoided due to the coupling.

The graphic elements can be reversibly coupled and decoupled, so that decoupled graphic elements can be separately modified. The physician or the technician thus can effect or cancel the coupling or grouping at any point in time, such that a very high degree of flexibility is provided with regard to the element positioning. The coupling can be effected or canceled via a suitable input unit, for example the typical computer mouse or a keyboard parameter input etc; similarly, the coupled element group can be adjusted (corrected) via this input unit.

In an embodiment of the invention, the graphic elements to be coupled can be selected by the user, so the physician or the technician has a free hand to determine via the input unit which graphic elements the user would like to couple for a subsequent interconnected repositioning. Alternatively, it is possible for all displayed graphic elements to be automatically coupled given selection of the coupling mode. This means that the coupling combination can be configured virtually arbitrarily.

As already described, graphic elements of different types can be used to establish the image acquisition parameters. Although, in principle, given a coupling of graphic elements of different types, a combination shift can be enabled via selection of an arbitrary group element. In a further embodiment, however, only one graphic element of a predetermined type can be selected as a graphic element whose position relationship will be followed by the coupled graphic elements coupled therewith so that with a given coupling, graphic elements of different types cannot be moved separately, or can be moved separately only with regard to the remaining coupled, positionally-fixed graphic elements. According to this inventive embodiment, the graphic elements are hierarchically organized dependent on their type; they can be differentiated as primary elements that are designated by an input selection as a position-determined element and secondary objects that cannot be selected. For example, only one such element can be selected as a graphic element with which the location of the image acquisition is determined, in particular in the form of a plane or a volume. Such a graphic element can be, for example, a 2D or 3D slice element, a volume element or a spatial grid via which the examination volume is defined. If such an element is thus contained within the group, it can be selected and the combination can be shifted dependent on the movement of this element. If other elements are coupled thereto that are classified as secondary elements (such as, for example, saturator elements), different embodiments are conceivable with regard to movement of the secondary elements. For example, it is possible that these graphic elements of different type are separately unmovable with a given coupling, meaning that it is not possible to reposition a saturator in an existing coupling. As an alternative, such elements may be moved separately while all other coupled elements remain positionally fixed. This is suitable, for example for the case of a number of 2D or 3D slice elements determining individual slices as well as a number of saturator elements being coupled within the group. Within the coupling, a slice element this group now can be selected as a primary element whose movement causes the entire combination to be moved therewith. However, if one of the saturator elements in a given coupling is moved, the remainder remains positionally fixed.

For some applications it would be sufficient, for example, to reposition only the graphic elements which cause the site of the image acquisition to be determined, for example while one or more already-positioned saturator elements remaining stationary. This is sometimes dependent on the type of the movement or the direction of the movement. For example, in a heart chamber image acquisition, in which a number of 2D slice elements are positioned in a star shape that intersect in the star center, by a rotation of the star-shaped arrangement around the center plane intersection point it is possible to rotate only the graphic elements determining the planes, while outer saturator elements surrounding them remain, so the entire combination follows given a longitudinal shift, in any direction. For this purpose, given a mutual movement of only one part of the coupled graphic elements, it can be appropriate to move only the similar graphic elements with the selected graphic element.

Overall, the inventive medical examination apparatus allows a significantly simpler, faster and more flexible adjustment of the image acquisition parameters. Positioning errors (for example accidental overlappings or a drifting of radial slices away from one another, etc.) can be prevented. The possibility also exists for real-time positioning of complex MR graphic element formations (structures). Some (but not exclusive) examples are:

a) the positioning of radial (star-shaped) slices, for example for heart or knee imaging, b) the positioning of three orthogonal slices, for example for a catheter tracking, in which the orthogonal slices are coupled with the catheter tip and the slices are automatically guided along in this manner given a catheter movement, such that a fly-through acquisition mode is possible during the movement of the catheter through a vessel, also in an interactive imaging or a heart imaging, c) the positioning of a CSI grid that is in particular bordered by saturation elements in all directions, in the framework of a CSI spectroscopy, d) the positioning of 2D or 3D slice elements attached to one another, for example for "Concatenated Scans" for peripheral angiography imaging or for whole-body examinations, as well as e) the positioning of saturation elements that lie parallel to 2D or 3D slices.

DESCRIPTION OF THE PREFERRED EMBODIMENTS

Figure 1:
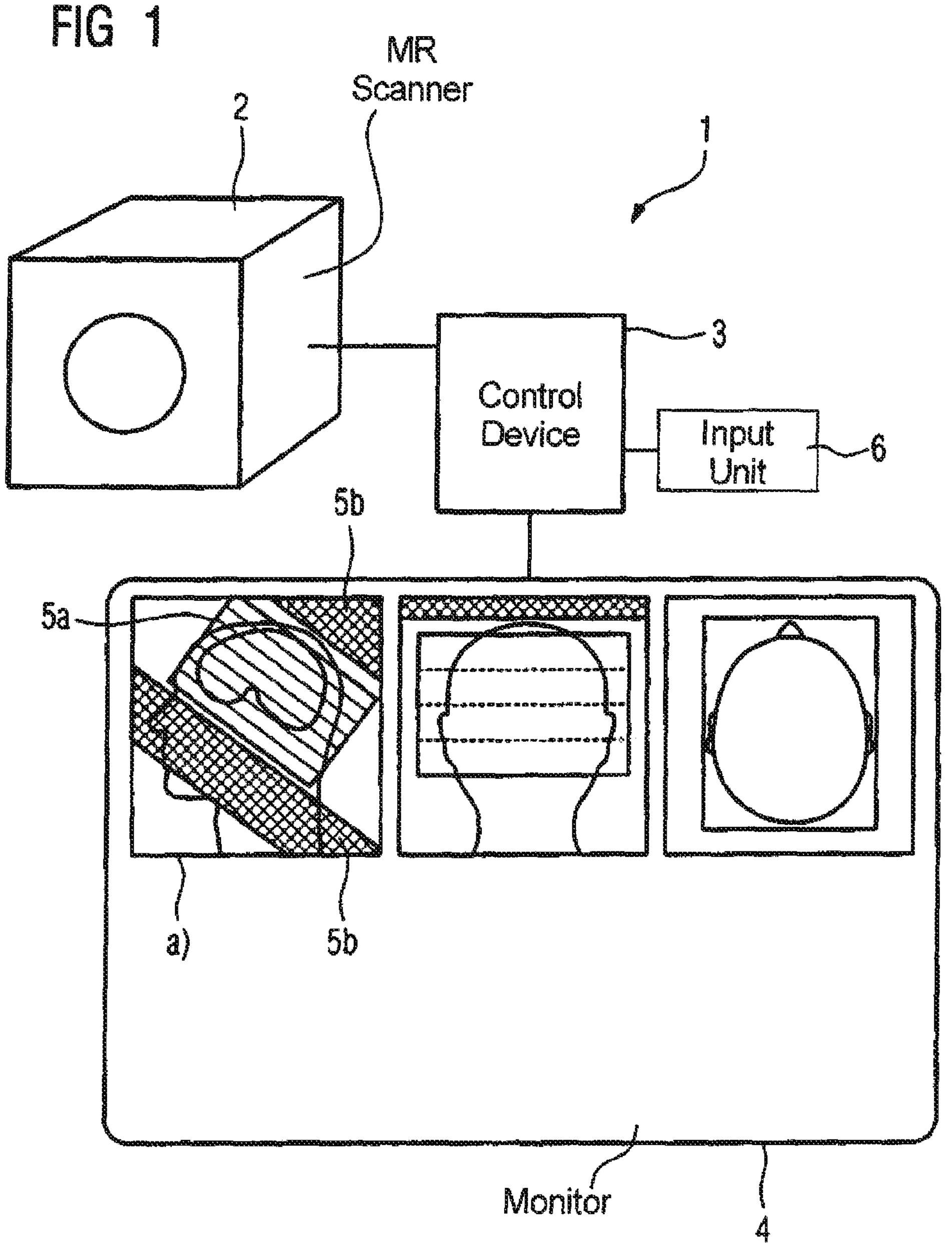
FIG. 1 is a block diagram of an inventive examination apparatus for explaining the procedure for adjustment of the slice image acquisition parameters.

FIG. 1 schematically illustrates an inventive examination apparatus 1 in the form of a magnetic resonance system with an MR scanner 2 for image (data) acquisition as well as a control device 3 with an associated monitor 4 on which acquired images can be displayed. Three exemplary slice images that sagittally, coronally and transversally show an examination subject (here the head of a patient) are displayed on the monitor 4. For subsequent scans, in order to be able to establish the image acquisition parameters with regard to the actual examination region and to be able to optimally determine these, the physician or the technician superimposes on the respective image exposure graphic elements with which are associated specific functions (which are "known" by the control device 3). These graphic elements allow adjustment of the image acquisition parameters that are subsequently put into effect by the control device 3. In the shown example, three graphic elements are illustrated in the image representation a), namely a first graphic element 5*a* which is, for example, a 3D slice element formed of a number of individual slices, via which 3D slice element the individual slices of the central examination subject of interest (here the brain) are defined. Two graphic elements 5*b* are shown above and below the 3D slice element 5*a*, the graphic elements 5*b* being saturator elements that cause the image regions defined by them to be shown black in the subsequently acquired image. Via an input unit 6 (which can be a computer mouse or a keyboard or the like), the user can select which graphic elements the user would like to have displayed; and the user can position these elements as needed. It is also possible for the user to couple the displayed elements with one another as needed in order to be able to position them according to combination as needed. This is subsequently described in different exemplary embodiments using FIGS. 2-4.

Figure 2:
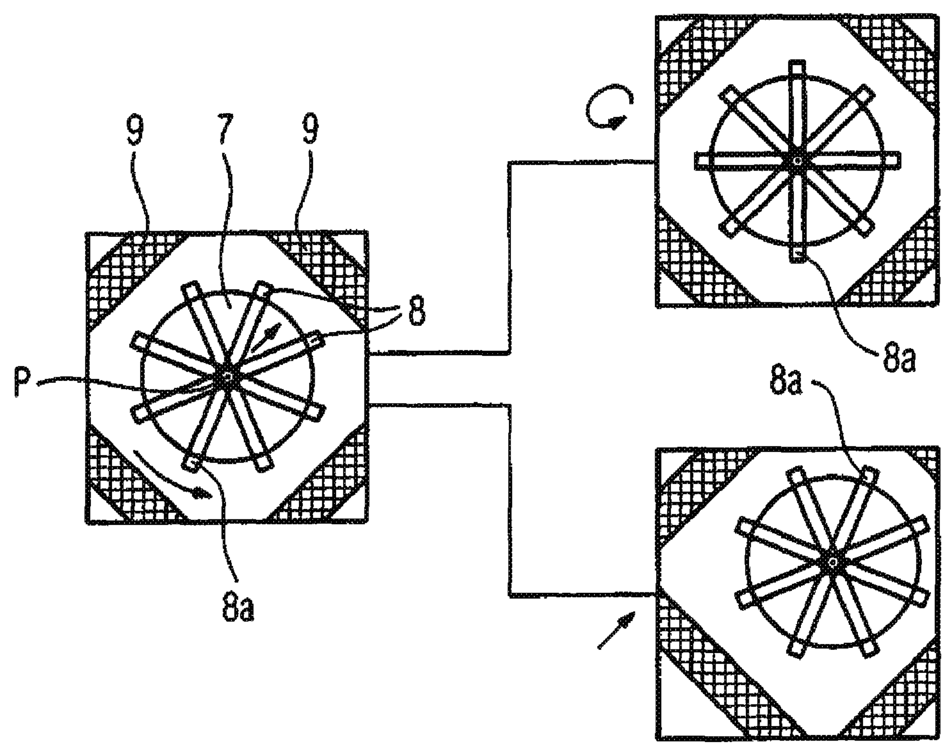
FIG. 2 shows an exemplary embodiment for element positioning after a preceding coupling, by movement of a selected graphic element.

FIG. 2 schematically shows an examination subject 7 displayed on a monitor, for example a short-axis representation of the left heart chamber. The physician already has positioned, in a star shape, a number (in the shown example, four) of graphic elements 8, which are all 2D slice elements; in a radial slice arrangement. The graphic elements 8 intersect in the center point P. Further graphic elements 9 in the form of individual saturator elements have been positioned at the corners.

If the user (physician) now determines that the star-shaped positioning selected by him or her is to be changed, via the input unit 6 the user can couple the graphic elements to one another with regard to their position relationship, for example by selection of a corresponding button that is shown on the monitor parallel to the image representation. The user can effect this coupling for all graphic elements 8, 9 or only, for example, for the graphic elements 8. The user thus can select this coupling given a corresponding configuration of the overall configuration. It is also possible for all displayed shown graphic elements to be always automatically coupled with one another.

Among the graphic elements 8, the physician now selects a slice element that he or she hereby defines as a primary element. In the shown example, the slice element 8*a* is selected. A selection of a graphic element 9 for designation thereof as a primary element is not possible because the configuration is such that only those elements that serve for the determination of the site of the slice image acquisition (such as, for example, the slice elements) are permissible for selection as primary elements.

The physician now has different possibilities as to how he or she can reposition the coupled combination. It is possible to rotate the star-shaped arrangement around its center point P, meaning that a purely rotational position change ensues. This is shown in the upper part in FIG. 2. By selection (for example with a mouse cursor), the slice element 8*a* is now rotated to the right by an angle $\alpha$ (shown by the arrow) into the position shown in the upper right image. All coupled slice elements 8 follow this rotational movement and change their position, but the position relationship of all slice elements 8 to one another remains the same, meaning that they to not change their angles with regard to one another. As the upper diagram in FIG. 2 shows, in this embodiment the positions of the graphic elements 9 remain positionally fixed, meaning that they are not moved in spite of the coupling. In this example, the mutual movement of these saturator elements is dependent on the movement direction or movement type. In the case of a pure rotational movement, a position change of the graphic elements 9 is not necessary, which is automatically detected by the control device 3, which is why the coupling is automatically, temporally emphasized (highlighted) dependent on movement.

An alternative to rotation is a longitudinal shift shown in the lower part in FIG. 2. In this case, for example after previous selection of the slice element 8*a* or the intersection point P, the entire coupled combination is shifted somewhat to the upper right, as shown by the arrow. In this case, all coupled elements (thus the graphic elements 8 and the graphic elements 9) are shifted somewhat to the upper right corresponding to the position change of the selected slice element 8*a*; the combination thus is moved as a whole.

Figure 3:
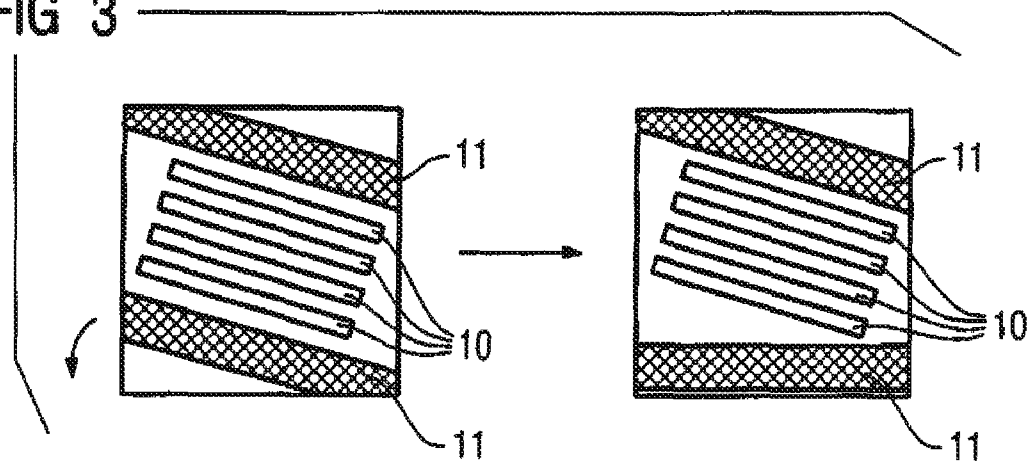
FIG. 3 illustrates a representation of the individual modification of a secondary graphic element with a given coupling.

FIG. 3 shows a further example. Here four graphic elements 10 have been positioned in a parallel arrangement, essentially in the form of 2D slice elements. Graphic elements 11 have been positioned as saturator elements respectively above and below the slice element combination. In order to be able to shift the entire combination, the physician would have to select a graphic element 10 and define it as a primary element. Given a rotation or shift, all coupled elements (namely the further slice graphic elements 10 and the coupled saturator graphic elements 11) would then follow the position change. If in the existing coupling it is desired that the entire combination not be moved, but rather (for example) only the lower slice element be somewhat rotated (as is shown by the arrow), the saturator graphic element 11 can be brought into a new position (as shown in FIG. 3 on the right) despite the existing coupling. Such a coupled graphic element (as long as it is not a designated primary element) can be adjusted in terms of position at any time, despite the existing coupling. As is shown on the right in FIG. 3, all other graphic elements are not changed in terms of position; only the lower, selected graphic element 11 is changed.

Figure 4:
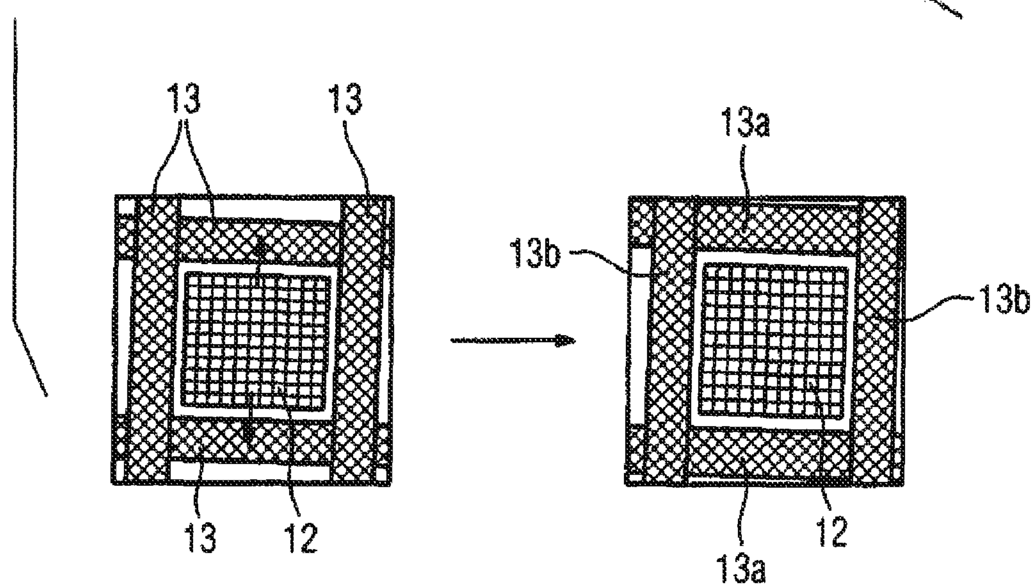
FIG. 4 illustrates an embodiment for modification of a CSI spatial grid.

FIG. 4 shows a further example in which a graphic element 12 is shown in the form of a CSI grid via which a volume is determined in the framework of CSI spectroscopy. CSI spectroscopy allows the determination of the chemical components within a selected volume that is defined by the CSI volume grid and that is itself comprised of a plurality of individual volume elements. Four further graphic elements 13 in the form of separate saturator elements are associated with the graphic element 12. If the physician now selects the coupling of the shown graphic elements 12, 13 and desires to enlarge the graphic element 12 (thus the CSI volume grid) as represented by both arrows, both saturator elements 13*a* follow due to the coupling. They are shifted upwardly or downwardly while both saturator elements 13*b* remain positionally fixed. The physician could now, for example, effect a lateral expansion in the same manner; in this case the saturator elements 13*b* would then be shifted outwardly.

It should be noted that any adjustment measure that provides the incorporation of information about the examination device from the examination subject or by the examination subject is encompassed within "adjustment of the image acquisition parameters". It does not have to be an image that is virtually displayed. Information processed, for example, in the framework of CSI spectroscopy can also be understood in the sense of an "image exposure".

In addition to the determination of primary elements that, due to their type, are suitable to be able to be actually selected and with whose positional change all coupled elements follow, as well as secondary elements that cannot be selected as elements on which to base the combination shift and that can be individually manipulated as secondary objects at any time by the user without having to release the entire combination or the combination having to follow, it is possible to define tertiary objects such as, for example, navigator rods or the like that generally cannot be included by the coupling mode. They cannot be incorporated into the element combination, thus in principle do not follow the changes of the primary object and can be individually positioned at any time (like a secondary object).

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical examination apparatus for acquiring slice images of a subject, comprising:

an image acquisition unit adapted to interact with a subject to acquire image data, representing an image of a slice, from the subject in an image acquisition procedure, said image of said slice representing a diagnostic tool for a medical diagnosis, and said medical diagnosis imposing conditions that dictate contents of said image acquisition procedure;

a control device connected to said image acquisition device that controls said image acquisition procedure, said control device comprising a display on which a plurality of graphic elements, representing selectable parameters that influence said image acquisition procedure, are displayed, and an input unit allowing a user to select one of said plurality of graphic elements as a primary graphic element and to selectively position said primary graphic element at said display;

said control device being configured to allow a coupling input to be made via said input unit that causes at least some of the displayed graphic elements, other than said primary graphic element to be coupled to said primary graphic element and to each other in terms of position on said display;

a position change on said display of the primary graphic element is made through said input unit, to cause all of said graphic elements coupled with said primary graphic element to be mutually moved on said display together with said primary graphic element while retaining a positional relationship on said display among all of the coupled elements, and said input unit allowing a subsequent decoupling input to be made that cancels the coupling caused by said coupling input, to thereafter allow decoupled graphic elements to be separately modified on said display by modifying inputs made through said input unit;

said control device being configured to limit inputs made via said input unit, to restrict graphic elements among said plurality of graphic elements that are permitted to be selected as said primary graphic element, dependent on said contents of said image acquisition procedure that are dictated by said medical diagnosis; and said control device being configured to generate control signals that operate said image acquisition unit corresponding to said positional relationship on said display among all of the coupled elements.

2. A medical examination apparatus as claimed in claim 1 wherein said control device is configured to limit inputs made via said input unit, to restrict graphic elements among said plurality of graphic elements that are permitted to be selected as said primary graphic element, dependent on a hierarchy of said contents of said image acquisition procedure that are dictated by said medical diagnosis.

3. A medical examination apparatus as claimed in claim 1 wherein said control device is configured to allow said coupling input to be configured, via said input unit, to individually select graphic elements on said display to be coupled with each other.

4. A medical examination apparatus as claimed in claim 1 wherein said control device is configured to automatically couple at least some of said graphic elements with each other dependent on information represented by the respective graphic elements.

5. A medical examination apparatus as claimed in claim 1 wherein said control device is configured to prevent an input, via said input unit, that attempts individual movement at said display of a remainder of graphic elements, other than said primary graphic element in said graphic elements that are coupled with each other.

6. A medical examination apparatus as claimed in claim 1 wherein said control device is configured to permit separate movement, via said input unit, of each of a remainder of said graphic elements, other than said primary graphic element, among said graphic elements coupled with one another, while retaining said positional relationship.

7. A medical examination apparatus as claimed in claim 1 wherein said control device is configured to permit selection, via said input unit, of only one primary graphic element that represents a designation of a site of acquisition of said image data in the subject.

8. A medical examination apparatus as claimed in claim 7 wherein said site is selected from the group consisting of a plane and a volume.

9. A medical examination apparatus as claimed in claim 7 wherein said primary graphic element designates a representation is selected from the group of representations consisting of a 2D slice element, a 3D slice element, a volume element and a spatial grid.

10. A medical examination apparatus as claimed in claim 1 wherein said control device is configured to generate said coupling so that mutual movement at said display, with movement of said primary graphic element, of at least some of said graphic elements coupled with said primary graphic element, ensues dependent on a movement type at said display of said primary graphic element.

11. A medical examination apparatus as claimed in claim 10 wherein said primary graphic element is a graphic element of a predetermined type, and wherein said control device is configured to generate said coupling so that said at least some of said graphic elements coupled with said primary graphic element are also of said predetermined type.

12. A medical examination apparatus as claimed in claim 1 wherein said control device is configured to generate said coupling so that mutual movement at said display, with movement of said primary graphic element, of at least some of said graphic elements coupled with said primary graphic element, ensues dependent on a movement direction at said display of said primary graphic element.

13. A medical examination apparatus as claimed in claim 12 wherein said selected graphic element is a graphic element of a predetermined type, and wherein said control device is configured to produce said coupling so that said at least some of said graphic elements coupled with said primary graphic element are also of said predetermined type.

* * * * *